United States Patent
Harsanyi et al.

(10) Patent No.: US 12,157,753 B2
(45) Date of Patent: Dec. 3, 2024

(54) PROCESS FOR PREPARING FOSTEMSAVIR

(71) Applicant: VIIV HEALTHCARE UK (No. 4) LIMITED, Stevenage (GB)

(72) Inventors: Antal Harsanyi, Stevenage (GB); Andrew David Searle, Stevenage (GB)

(73) Assignee: ViiV Healthcare UK (No.4) Limited (GB)

( * ) Notice: Subject to any disclaimer, the term of this patent is extended or adjusted under 35 U.S.C. 154(b) by 740 days.

(21) Appl. No.: 17/421,851

(22) PCT Filed: Jan. 15, 2020

(86) PCT No.: PCT/IB2020/050312
§ 371 (c)(1),
(2) Date: Jul. 9, 2021

(87) PCT Pub. No.: WO2020/148679
PCT Pub. Date: Jul. 23, 2020

(65) Prior Publication Data
US 2022/0106341 A1    Apr. 7, 2022

Related U.S. Application Data

(60) Provisional application No. 62/793,462, filed on Jan. 17, 2019.

(51) Int. Cl.
*C07D 471/04* (2006.01)
*C07D 491/04* (2006.01)
*C07F 9/6561* (2006.01)

(52) U.S. Cl.
CPC .......... *C07F 9/6561* (2013.01); *C07D 471/04* (2013.01); *C07D 491/04* (2013.01)

(58) Field of Classification Search
CPC .... C07F 9/6561; C07D 471/04; C07D 491/04
See application file for complete search history.

(56) References Cited

FOREIGN PATENT DOCUMENTS

CN    105669686 A    6/2016
EP    2141168 A1    1/2010

OTHER PUBLICATIONS

Bultman, et al., "Preparation of the HIV Attachment Inhibitor BMS-663068. Part 4. Synthesis of the 6-Azaindole Core", Organic Process Research and Development; vol. 21, No. 8; Aug. 18, 2017 (Aug. 18, 2017); pp. 1131-1136.
Meanwell, et al., "Inhibitors of HIV-1 Attachment: The Discovery and Development of Temsavir and its Prodrug Fostemsavir", Journal of Medicinal Chemistry; vol. 61, No. 1; Jan. 11, 2018 (Jan. 11, 2018); pp. 62-80.
Schneider, et al., "Acid-catalysed cyclization of 1-aryl-2-thienylmethyl- and 1-aryl-2-furfuryl-aminoethanols via spiro intermediates", Journal of the Chemical Society, Perkin Transactions 1; Jan. 1, 1986 (Jan. 1, 1986); pp. 877-883.

*Primary Examiner* — Susanna Moore
(74) *Attorney, Agent, or Firm* — W. Brett Stauffer

(57) ABSTRACT

A method for the preparation of a compound of Formula IV

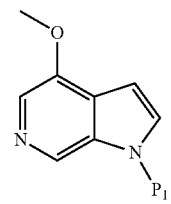

Formula IV wherein $P^1$ is H or a suitable protecting group, comprising preparation of a compound of Formula I

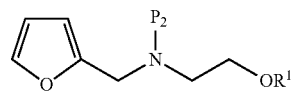

Formula I wherein $P^2$ is H or a suitable protecting group and $R^1$ is H or $C_{1-6}$alkyl.

18 Claims, No Drawings

PROCESS FOR PREPARING FOSTEMSAVIR

This application is a § 371 of International Application No. PCT/IB2020/050312, filed 15 Jan. 2020, which claims the benefit of U.S. Provisional Application No. 62/793,462, filed 17 Jan. 2019.

FIELD OF THE INVENTION

The present invention relates to a process for preparing Fostemsavir.

BACKGROUND OF THE INVENTION

HIV infection remains a major medical problem. One class of compounds with potential for treating HIV infection are HIV attachment inhibitors. These are compounds that bind to the HIV surface glycoprotein gp120 and interfere with the interaction between the surface protein gp120 and the host cell receptor CD4. Thus, they prevent HIV from attaching to the human CD4 T-cell and block HIV replication in the first stage of the HIV life cycle.

One HIV attachment inhibitor compound that has shown promise as a treatment for HIV infection is Fostemsavir. Fostemsavir is described, for example in U.S. Pat. No. 7,745,625. Methods for preparing Fostemsavir are described, for example, in the '625 patent and in WO2012/106189, WO2013/119625, and WO2016/100633.

Fostemsavir is a prodrug of Temsavir. Temsavir is described, for example, in U.S. Pat. No. 7,354,924. Methods for preparing Temsavir are described, for example, in the '924 patent and in WO2007/002308.

An intermediate in the preparation of Temsavir and Fostemsavir is the following compound

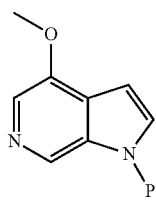

where P is a suitable protecting group such as mesylate, tosylate, or besylate.

SUMMARY OF THE INVENTION

Briefly, in one aspect, the present invention discloses a method for preparation of a compound of Formula IV

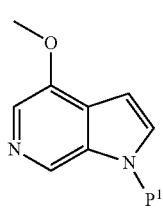

Formula IV wherein $P^1$ is H or a suitable protecting group;

comprising the preparation of a compound of Formula I

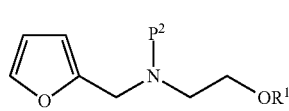

Formula I wherein $P^2$ is H or a suitable protecting group and $R^1$ is H or $C_{1-6}$alkyl.

Compounds of Formula IV can be converted to Temsavir, Fostemsavir, and various salts thereof using known methods, for examples those referenced in the Background section.

DETAILED DESCRIPTION OF THE INVENTION

Preferably, the method of this invention further comprises the conversion of a compound of Formula I to a compound of Formula II

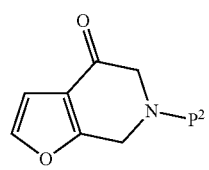

Formula II wherein each $P^2$ is independently H or a suitable protecting group.

Preferably, the method of this invention further comprises the conversion of a compound of Formula II into a compound of Formula III

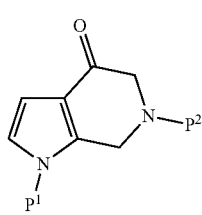

Formula III wherein each $P^1$ and $P^2$ are independently H or a suitable protecting group.

Protecting groups are well known in the art and a chemist skilled in the art would be able to choose appropriate protecting groups.

Preferably $P^1$ is H or a sulphonyl group. More preferably $P^1$ is H or a mesylate, besylate, or tosylate group.

Preferably $P^2$ is H or an alkyloxycarbonyl, aryloxycarbonyl, acetyl optionally substituted with 1-3 halogens, sulphonyl, alkyl, $C_{1-6}$alkyl, or benzyl group. More preferably $P^2$ is H or —C(O)—O—$C_{1-4}$alkyl, —C(O)—$C_{1-4}$alkyl, —C(O)—$C_{1-4}$haloalkyl, mesylate, besylate, tosylate, $C_{1-6}$alkyl, or —$C_{1-6}$alkyl-aryl.

EXAMPLES
One embodiment of the method of this invention can be summarized by the following reaction scheme.
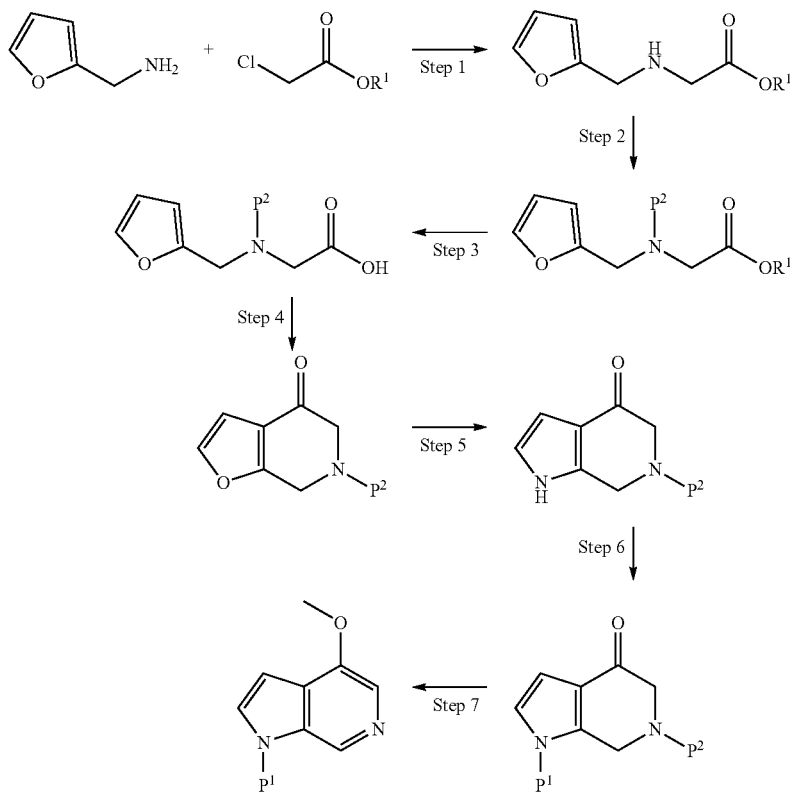
The method of this invention is further illustrated by the following examples. Examples 1, 2 and 3 are summarized in the three schemes below:
Example 1
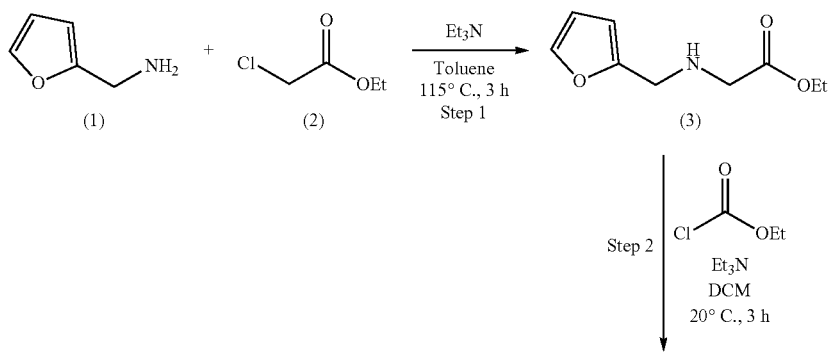

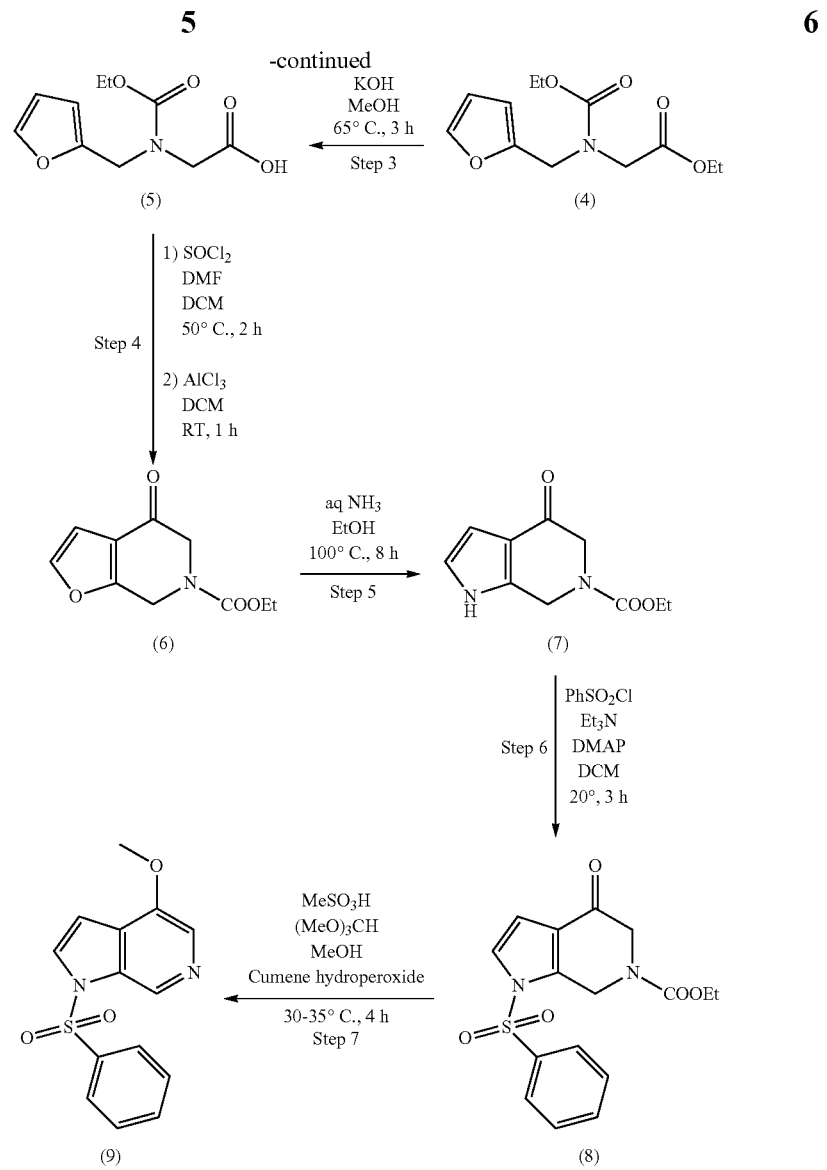
Example 2
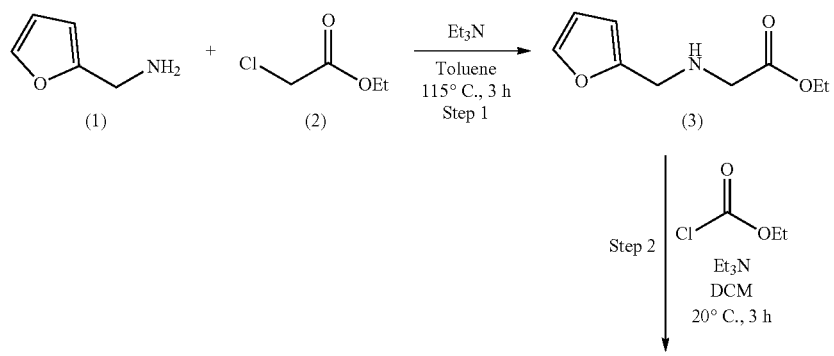

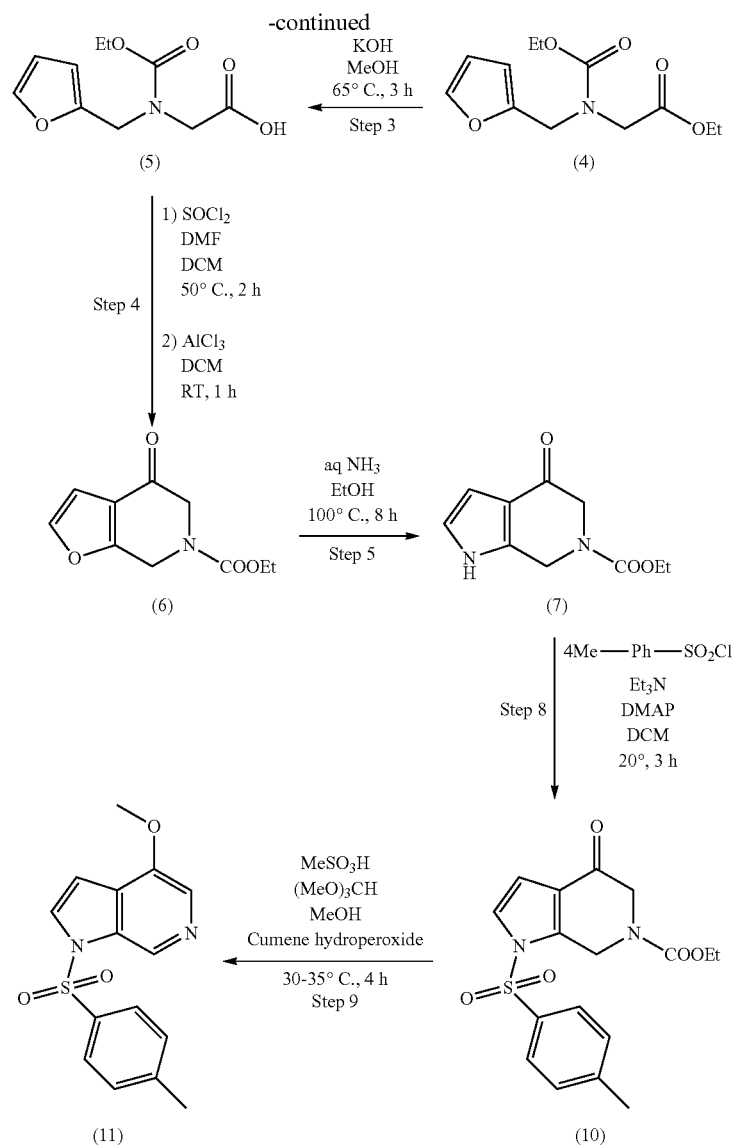
Example 3
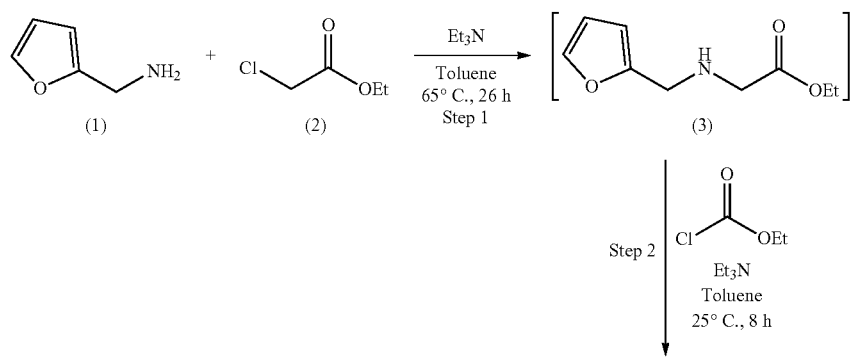

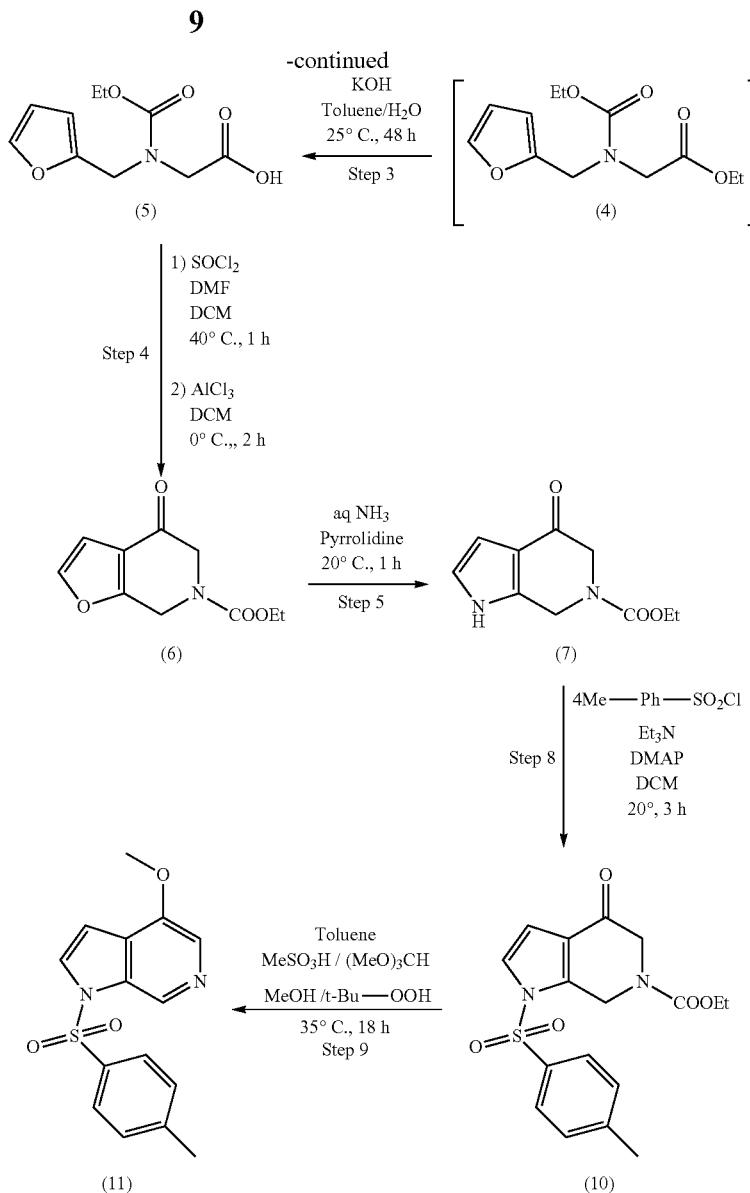

As a general summary of an embodiment of the method of this invention, a compound of Formula 1 can be prepared from furfurylamine and a protected chloroacetate (for example. ethyl chloroacetate) in the presence of a suitable base followed by protection with a suitable reagent (for example, ethyl chloroformate) in the presence of a suitable base (for example, triethylamine). A compound of Formula I can be converted to a compound of Formula II by hydrolysis in the presence of a suitable base (for example, potassium hydroxide), followed by formation of an acid chloride which can be cyclised using a suitable catalyst (for example, Aluminium Chloride). A compound of Formula II can be converted to a compound of Formula III by reaction with ammonia or an ammonia equivalent in the presence of a secondary amine reagent, for example pyrrolidine followed by protection with a suitable reagent (for example, benzenesulfonyl chloride or 4-methylbenzenesulfonyl chloride) in the presence of a suitable base (for example, triethylamine). A compound of Formula III can be converted to a compound of Formula IV by conversion to the corresponding methyl enol ether and oxidation with a suitable reagent (for example, Cumene Hydroperoxide or tert-butyl hydroperoxide.

Example 1

Step 1: Preparation of ethyl 2-((furan-2-ylmethyl)amino)acetate (3)

Furfurylamine (1) (5.50 mL, 51.5 mmol) and triethylamine (7.90 mL, 56.5 mmol, 1.1 eqv) were dissolved in toluene (27.5 mL, 5 vols.). Ethyl chloroacetate (2) (6.05 mL, 56.5 mmol, 1.1 eqv) was added and the mixture was heated to 115° C. for 3 hours. Reaction was then cooled to 20° C., water (33 mL, 6 vols.) was added and the mixture was extracted with ethyl acetate (3×27.5 mL, 3×5 vols.). The organic layer was washed with water (2×27.5 mL, 2×5 vols.) and a saturated brine solution of (27.5 mL, 5 vols.), then dried over anhydrous magnesium sulphate, filtered and the solvent was evaporated in vacuo to give ethyl 2-((furan-2-ylmethyl)amino)acetate (3) as a yellow liquid (7.15 g, 42.8 mmol, 75.8% yield). ¹H NMR (600 MHz, DMSO-d₆, 300K): δ 7.55 (1H, dd, J=1.8 Hz, 0.9 Hz), 6.34 (1H, dd, J=3.1 Hz, 1.8 Hz), 6.22 (1H, dd, J=3.1 Hz, 0.9 Hz), 4.08 (2H, q, J=7.2 Hz), 3.70, (2H, s), 3.29 (2H, s), 1.19 (3H, t, J=7.2 Hz). ¹³C{¹H} NMR (151 MHz, DMSO-d₆, 300K): δ172.4, 154.2, 142.4, 110.7, 107.4, 60.4, 49.7, 45.1, 14.6. HRMS (ESI) m/z [M+H]⁺: molecular ion calculated for $C_9H_{14}NO_3$: 184.0968, found 184.0974, error 3.4 ppm. (3) can be further purified by column chromatography—normal phase on silica gel, 0-20% gradient of methanol in methylene chloride.

Ethyl 2-((furan-2-ylmethyl)amino)acetate(3) (5.00 g, 27.3 mmol) and triethylamine (4.55 mL, 32.8 mmol, 1.2 eqv) were dissolved in methylene chloride (5 mL, 1 vol.). Ethyl chloroformate (2.24 mL, 32.8 mmol, 1.2 eqv) was added dropwise at 0° C. (reaction temperature NGT 25° C.) and the mixture was stirred at 20° C. for 3 hours. Water (25 mL, 5 vols.) was added and the mixture was extracted with methylene chloride (2×25 mL, 2×5 vols.). The organic layer was washed with water (2×25 mL, 2×5 vols.) and a saturated brine (1×25 mL, 5 vols.), dried over anhydrous magnesium sulphate, filtered and the solvent was evaporated in vacuo to leave ethyl 2-((ethoxycarbonyl)(furan-2-ylmethyl)amino) acetate (4) as a dark brown oil (6.41 g, 25.14 mmol, 92.1% yield). ¹H NMR (600 MHz, DMSO-d₆, 300K). [Note: at this temperature, two rotamers (A+B) in an approximately eqvual ratio are visible. They are due to restricted rotation of the tertiary amide: δ 7.60-7.58 (A+B, 1H, m), 6.40-6.38, (A+B, 1H, m), 6.36 (A, 1H, d, J=3.2 Hz), 6.33 (B, 1H, d, J=3.2 Hz), 4.46 (A+B, 2H, s), 4.09 (B, 2H, q, J=7.0 Hz)), 4.08, (A+B, 2H, q, J=7.7 Hz), 4.04, (A, 2H, q, J=7.0 Hz) 3.94, (A+B, 2H, s), 1.20 (B, 3H, t, J=7.0 Hz), 1.17 (A+B, 3H, t, J=7.1 Hz), 1.13 (B, 3H, t, J=7.0 Hz). ¹³C{¹H} NMR (151 MHz, DMSO-d₆, 300K): δ 169.7 (A), 169.6 (B), 159.9 (B), 155.8 (A), 151.1 (B), 151.0 (A), 143.3 (A), 143.2 (B), 110.9 (B), 110.8 (A), 109.1 (A), 108.8 (B), 61.8 (B), 61.6 (A), 61.03 (A), 60.98 (B), 48.5 (B), 48.2 (A), 44.3 (A), 44.2 (B), 14.90 (B), 14.85 (A), 14.5 (A+B). HRMS (ESI) m/z [M+H]⁺: molecular ion calculated for $C_{12}H_{18}NO_5$: 256.1179, found 256.1184, error 1.9 ppm. (4) can be further purified by column chromatography—normal phase on silica gel, 0-60% gradient of ethyl acetate in hexane.

Step 3: Preparation of 2-((ethoxycarbonyl)(furan-2-ylmethyl)amino)acetic acid (5)

Ethyl 2-((ethoxycarbonyl)(furan-2-ylmethyl)amino)acetate (4) (5.00 g, 19.6 mmol) was dissolved in methanol (25 ml, 5 vols.), potassium hydroxide (1.65 g, 29.4 mmol, 1.5 eqv) was added and the mixture was heated at 65° C. for 3 hours. The solvent was evaporated in vacuo and the residue was dissolved in methylene chloride (50 mL, 10 vols.). The resulting solution was slowly neutralized with 1N aqueous solution of hydrochloric acid with stirring to adjust to pH 3. The organic layer was separated, washed with water (2×25 mL, 2×5 vols.) and a saturated brine solution of (1×25 mL, 5 vols.), dried over anhydrous magnesium sulphate, filtered and the solvent evaporated in vacuo to leave 2-((ethoxycarbonyl)(furan-2-ylmethyl)amino)acetic acid (5) as a dark brown oil (4.23 g, 18.6 mmol, 95.1% yield). ¹H NMR (600 MHz, DMSO-d₆, 300K). [Note: at this temperature, two rotamers (A+B) in an approximately equal ratio are visible. They are due to restricted rotation of the tertiary amide: δ 7.60-7.58 (A+B, 1H, m), 6.40-6.38, (A+B, 1H, m), 6.36 (A, 1H, d, J=3.0 Hz), 6.34 (B, 1H, d, J=3.0 Hz), 4.44 (A+B, 2H, s), 4.08 (B, 2H, q, J=7.0 Hz), 4.03, (A, 2H, q, J=7.0 Hz) 3.83 (B, 2H, s), 3.82 (A, 2H, s), 1.20 (B, 3H, t, J=7.0 Hz), 1.14 (A, 3H, t, J=7.0 Hz). ¹³C{¹H} NMR (151 MHz, DMSO-d₆, 300K): δ 171.1 (A), 171.0 (B), 156.0 (A), 155.9 (B), 151.2 (B), 151.1 (A), 143.3 (A), 143.2 (B), 110.91 (B), 110.88 (A), 109.1 (A), 108.8 (B), 61.7 (B), 61.6 (A), 61.03 (A), 48.3 (B), 47.9 (A), 44.2 (A), 44.1 (B), 14.94 (B), 14.91 (A). HRMS (ESI) m/z [M+Na]⁺: molecular ion calculated for $C_{10}H_{13}NNaO_5$: 250.0686, found 250.0681, error 1.9 ppm. (5) can be further purified by column chromatography—normal phase on silica gel, 0-20% gradient of methanol in methylene chloride.

Step 4: Preparation of ethyl 4-oxo-4,5-dihydrofuro[2,3-c]pyridine-6(7H)-carboxylate (6)

2-((Ethoxycarbonyl)(furan-2-ylmethyl)amino)acetic acid (5) (4.00 g, 17.6 mmol) was dissolved in methylene chloride (60 mL, 15 vols.), thionyl chloride (1.92 mL, 26.4 mmol, 1.5 eqv) and dimethylformamide (0.014 mL, 0.18 mmol, 0.01 eqv) were added and the mixture was heated at 50° C. for 3 hours. The reaction was cooled and diluted with methylene chloride (120 mL, 30 vols.), and aluminium chloride (4.69 g, 35.2 mmol, 2 eqv) was added. The mixture was stirred at 20° C. for 1 hour. The reaction mixture was poured over ice water (120 mL, 30 vols.), the organic layer was separated, washed with water (2×40 mL, 2×10 vols) and a saturated brine solution (1×40 mL, 10 vols.), dried over anhydrous magnesium sulphate, filtered and the solvent evaporated in vacuo. The residue was dissolved in ethyl acetate (40 mL, 10 vols.), washed with 5% aqueous ammonia (1×20 mL, 5 vols.) and then water (3×20 mL, 2×5 vols) and the solvent evaporated in vacuo. The residue solidified to give ethyl 4-oxo-4,5-dihydrofuro[2,3-c]pyridine-6(7H)-carboxylate (6) as yellow/orange solid (2.14 g, 10.2 mmol, 58.0% yield). ¹H NMR (600 MHz, DMSO-d₆, 300K). [Note: at this temperature, two rotamers (A+B) in an approximately eqvual ratio are visible. They are due to restricted rotation of the tertiary amide: δ 7.86 (A+B, 1H, d, J=2.0 Hz), 6.80 (A+B, 1H, d, J=2.0 Hz), 4.81 (A+B, 2H, br s), 4.17 (A+B, 2H, br s), 4.11 (A+B, 2H, q, J=7.1 Hz), 1.21 (A+B, 3H, t, J=7.1 Hz). ¹³C{¹H} NMR (151 MHz, DMSO-d₆, 300K): δ 188.3 (A+B), 163.7 (A), 163.4 (B), 154.6 (A+B), 144.9 (A+B), 119.1 (A+B), 105.9 (A+B), 61.8 (A+B), 51.7 (A), 51.5 (B), 41.3 (A+B), 14.4 (A+B). HRMS (ESI) m/z [M+H]⁺: molecular ion calculated for $C_{10}H_{12}NO_4$: 210.0761, found 210.0767, error 3.0 ppm.

Step 5: Preparation of ethyl 4-oxo-4,5-dihydro-1H-pyrrolo[2,3-c]pyridine-6(7H)-carboxylate (7)

Ethyl 4-oxo-4,5-dihydrofuro[2,3-c]pyridine-6(7H)-carboxylate (6) (2.00 g, 9.55 mmol) was dissolved in ethanol (10 mL, 5 vols.) and transferred to pressure vessel. 25% aq. ammonia (10 mL, 5 vols.) was added, the vessel was sealed, heated to 100° C. (reaction temperature 95° C.) and stirred for 8 hours. The ethanol was removed in vacuo and methylene chloride (10 mL, 5 vols.) was added to the residue. A black precipitate was filtered off and the filtrate was evaporated in vacuo, to leave ethyl 4-oxo-4,5-dihydro-1H-pyrrolo[2,3-c]pyridine-6(7H)-carboxylate (7) as a dark brown oil (1.77 g, 8.50 mmol, 89.0% yield). ¹H NMR (600 MHz, DMSO-d₆, 300K). [Note: at this temperature, two rotamers (A+B) in an approximately equal ratio are visible. They are due to restricted rotation of the tertiary amide: δ 11.58 (A, 1H, s), 11.53 (B, 1H, s), 6.87-6.88 (A+B, 1H), 6.36 (A+B, 1H, dd, J=2.2 Hz, 2.8 Hz), 4.70 (A+B, 2H, br s), 4.09 (A+B, 2H, q, J=7.1 Hz), 4.06 (A+B, 2H, br s), 1.20 (A+B, 3H, t, J=7.1 Hz). ¹³C{¹H} NMR (151 MHz, DMSO-d₆, 300K): δ 188.0 (A), 187.8 (B), 155.2 (A), 155.1 (B), 140.9 (A), 140.5 (B), 120.8 (A+B), 118.2 (A), 118.0 (B), 104.9 (A+B), 61.9 (A+B), 52.2 (A), 52.0 (B), 41.1 (A), 41.0 (B), 14.9 (A+B). HRMS (ESI) m/z [M+H]$^+$: molecular ion calculated for $C_{10}H_{13}N_2O_3$: 209.0921, found 209.0929, error 3.9 ppm. (7) may be further purified by column chromatography—normal phase on silica gel, 12-100% gradient of ethyl acetate in hexane.

Step 6: Preparation of ethyl 4-oxo-1-(phenylsulfonyl)-4,5-dihydro-1H-pyrrolo[2,3-c]pyridine-6(7H)-carboxylate (8)

To a solution of (ethyl 4-oxo-4,5-dihydro-1H-pyrrolo[2,3-c]pyridine-6(7H)-carboxylate) (7) (0.50 g, 2.4 mmol) in methylene chloride (5 mL, 10 vols.) was added triethylamine (0.97 mL, 7.2 mmol, 3 eqv.) dropwise at 20° C. To the resulting suspension was added benzene sulphonyl chloride (0.306 mL, 2.4 mmol, 1 eqv) and 4-dimethylaminopyridine (DMAP) (0.029 g, 0.24 mmol, 0.1 eqv). The reaction mixture was stirred until benzene sulphonyl chloride was consumed. The mixture was poured into water (10 mL, 20 vols.) and extracted with methylene chloride (2×5 mL, 10 vols. each). Combined organic layers were dried over anhydrous magnesium sulphate, filtered and evaporated in vacuo. The crude was purified by flash chromatography on silica gel (12-100% gradient ethyl acetate in hexane) affording ethyl 4-oxo-1-(phenylsulfonyl-4,5-dihydro-1H-pyrrolo[2,3-c]pyridine-6(7H)-carboxylate (8) as a yellow semi-solid (0.56 g, 1.61 mmol, 67.0% yield). $^1$H NMR (600 MHz, DMSO-d$_6$, 300K). [Note: at this temperature, two rotamers (A+B) in an approximately eqvual ratio are visible. They are due to restricted rotation of the tertiary amide: δ 8.08 (A+B, 2H, d, J=8.0 Hz), 7.86 (A+B, 1H, t, J=8.0 Hz), 7.74 (A+B, 2H, t, J=8.0 Hz), 7.58 (A+B, 1H, d, J=3.2 Hz), 6.66 (A+B, 1H, d, J=3.2 Hz), 4.99 (A+B, 2H, s), 4.16 (A+B, 2H, br s), 4.06 (A+B, 2H br q, J=7.0 Hz), 1.17 (A+B, 3H, br t, J=7.0 Hz). $^{13}$C{$^1$H} NMR (151 MHz, DMSO-d$_6$, 300K): δ 189.1 (A), 188.7 (B), 155.2 (A), 155.0 (B), 141.3 (A), 140.9 (B), 137.3 (A+B), 136.2 (A+B), 130.9 (A+B), 127.6 (A+B), 123.8 (A+B), 122.9 (A), 122.7 (B), 109.0 (A+B), 62.3 (A+B), 52.0 (A+B), 41.7 (A), 41.3 (B), 14.9 (A+B). HRMS (ESI) m/z [M+H]$^+$: molecular ion calculated for $C_{16}H_{17}N_2O_5S$: 349.0853, found 349.0857, error 1.1 ppm.

Step 7: Preparation of 4-methoxy-1-(phenylsulfonyl)-1H-pyrrolo[2,3-c]pyridine (9)

Ethyl 4-oxo-1-(phenylsulfonyl)-4,5-dihydro-1H-pyrrolo[2,3-c]pyridine-6(7H)-carboxylate (8) (0.50 g, 1.44 mmol) was charged to reaction vessel and vessel was inerted using N$_2$. Methanol (6 mL, 12 vols.), methane sulphonic acid (0.109 mL, 2.16 mmol, 1.5 eqv,) and trimethylorthoformate (0.788 mL, 7.2 mmol, 5 eqv) were added and reaction mixture was heated to 30-35° C. and aged for 2 hours. 80% Cumene hydroperoxide (CHP) (0.064 mL, 0.345 mmol, 0.25 eqv) was added and the reaction mixture was aged at 30-35° C. for 2-3 hours. Another 80% CHP (0.067 mL, 0.36 mmol, 0.25 eqv) was added and the reaction mixture was aged at 30-35° C. for 2-3 hours. A further charge of 80% CHP (0.067 mL, 0.36 mmol, 0.25 eqv), was added, the reaction was aged for 1 hour. This was repeated as required until reaction went to completion. The mixture was cooled to 20° C. Triethylamine (0.506 mL, 3.6 mmol, 2.5 eqv) was added at a rate to maintain the internal temperature at 30° C., and pH was confirmed in range 8-9. 1 wt % aqueous sodium thiosulphate solution (2 mL, 4 vols.) was added and the batch aged for 1 hour. 1 wt % aqueous sodium thiosulphate solution (8 mL, 16 vols.) was added over 30 minutes. The batch was aged for 1 hour, and the pH was confirmed as Methylene chloride (15 mL, 30 vols.) was added to the reaction mixture, and the layers were separated. The aqueous layer was washed with methylene chloride (2×5 mL, 2×10 vols.) and the combined organic layers were washed with 1M sodium hydroxide (2×5 mL, 2×10 vols) and water (1×5 mL, 10 vols). The combined organic layers were dried over anhydrous magnesium sulphate, filtered and evaporated in vacuo to leave a brown oil which was purified by column chromatography (12-100% gradient ethyl acetate in hexane) to give 4-methoxy-1-(phenylsulfonyl)-1H-pyrrolo[2,3-c]pyridine (9) as a yellow solid (0.345 g, 1.20 mmol, 83.0% yield). $^1$H NMR (600 MHz, DMSO-d$_6$, 300K): δ 8.89 (1H, s), 8.12 (1H, s), 8.06-8.09 (2H, m), 7.97 (1H, d, J=3.7 Hz), 7.73 (1H, tt, J=7.5 Hz, 1.1 Hz), 7.64-7.61 (2H, m), 6.90 (1H, d, J=3.7 Hz), 3.96 (3H, s). $^{13}$C{$^1$H} NMR (151 MHz, DMSO-d$_6$, 300K): δ 149.2, 137.2, 135.6, 132.4, 130.5, 129.5, 128.8, 127.4, 126.3, 125.6. 105.9, 56.7. HRMS (ESI) m/z [M+H]$^+$: molecular ion calculated for $C_{14}H_{13}N_2O_3S$: 289.0641, found 289.0644, error 1.0 ppm.

Example 2

Steps 1-7 are the same as for Example 1

Step 8: Preparation of ethyl 4-oxo-1-tosyl-4,5-dihydro-1H-pyrrolo[2,3-c]pyridine-6(7H)-carboxylate (10)

To a solution of (ethyl 4-oxo-4,5-dihydro-1H-pyrrolo[2,3-c]pyridine-6(7H)-carboxylate) (7) (0.50 g, 2.4 mmol) in methylene chloride (5 mL, 10 vols.) was added triethylamine (0.97 mL, 7.2 mmol, 3 eqv) dropwise at room temperature. To the resulting suspension was added p-toluenesulphonyl chloride (0.46 g, 2.4 mmol, 1 eqv) and 4-dimethylaminopyridine (DMAP) (0.029 g, 0.24 mmol, 0.1 eqv). The reaction mixture was stirred until p-toluenesulphonyl chloride was consumed. The mixture was poured into water (10 mL, 20 vols.) and extracted with methylene chloride (2×5 mL, 2×10 vols.). Combined organic layers were dried over anhydrous magnesium sulphate, filtered and evaporated in vacuo. The crude was purified by flash chromatography on silica gel (10% ethyl acetate in cyclohexane) affording ethyl 4-oxo-1-tosyl-4,5-dihydro-1H-pyrrolo[2,3-c]pyridine-6(7H)-carboxylate (10) as a pale pink solid (0.58 g, 2.0 mmol, 83.0% yield). $^1$H NMR (600 MHz, DMSO-d$_6$, 300K). [Note: at this temperature, two rotamers (A+B) in an approximately equal ratio are visible. They are due to restricted rotation of the tertiary amide: δ 7.96 (A+B, 2H, d, J=8.3 Hz), 7.55-7.53 (A+B, 3H, m), 6.64 (A+B, 1H, d, J=3.5 Hz), 4.98 (A+B, 2H, s), 4.13 (A+B, 2H, br s), 4.07 (A+B, 2H br q, J=7.0 Hz), 2.42 (3H, s), 1.17 (A+B, 3H, br t, J=7.0 Hz). $^{13}$C{$^1$H} NMR (151 MHz, DMSO-d$_6$, 300K): δ 189.1 (A), 188.6 (B), 155.2 (A), 155.0 (B), 147.3 (A+B), 141.1 (A), 140.7 (B), 134.3 (A+B), 131.1 (A+B), 127.7 (A+B), 123.9 (A+B), 122.8 (A), 122.6 (B), 108.8 (A+B), 62.3 (A+B), 51.9 (A+B), 41.6 (A), 41.4 (B), 21.6 (A+B), 14.8 (A+B). HRMS (ESI) m/z [M+H]$^+$: molecular ion calculated for $C_{17}H_{19}N_2O_5S$: 363.1009, found 363.1017, error 2.2 ppm.

Step 9: Preparation of 4-methoxy-1-(4-methylphenylsulphonyl)-1H-pyrrolo[2,3-c]pyridine (11)

(Ethyl 4-oxo-1-tosyl-4,5-dihydro-1H-pyrrolo[2,3-c]pyridine-6(7H)-carboxylate) (10) (0.50 g, 1.38 mmol) was charged to reaction vessel and vessel was inerted using N$_2$. Methanol (6 mL, 12 vols.), methane sulphonic acid (0.104 mL, 1.60 mmol, 1.15 eqv,) and trimethylorthoformate (0.755 mL, 6.9 mmol, 5 eqv) were added and reaction mixture was heated to 30-35° C. and aged for 2 hours. 80% Cumene hydroperoxide (CHP) (0.064 mL, 0.345 mmol, 0.25 eqv) was added and the reaction mixture was aged at 30-35° C. for 2-3 hours. Another 80% CHP (0.064 mL, 0.345 mmol, 0.25 eqv) was added and the reaction mixture was aged at 30-35° C. for 2-3 hours. A further charge of 80% CHP (0.064 mL, 0.345 mmol, 0.25 eqv), was added, the reaction was aged for 1 hour. This was repeated as required until reaction went to completion. The mixture was cooled to 20° C. Triethylamine (0.485 mL, 3.45 mmol, 2.5 eqv) was added at a rate to maintain the internal temperature at ≤30° C., and pH was confirmed in range 8-9. 1 wt % aqueous sodium thiosulphate solution (2 mL, 4 vols.) was added and the batch aged for 1 hour. 1 wt % aqueous sodium thiosulphate solution (8 mL, 16 vols.) was added over 30 minutes. The batch was aged for 1 hour, and the pH was confirmed as Methylene chloride (15 mL, 30 vols.) was added to the reaction mixture, and the layers were separated. The aqueous layer was washed with methylene chloride (2×5 mL, 2×10 vols.) and the combined organic layers were washed with water (2×5 mL, 2×5 vols) and saturated brine solution (2×25 mL, 2×5 vols). The combined organic layers were dried over anhydrous magnesium sulphate, filtered and evaporated in vacuo to leave a brown oil which was purified by column chromatography (12-100% gradient ethyl acetate in hexane) to give 4-methoxy-1-(4-methylphenylsulphonyl)-1H-pyrrolo[2,3-c]pyridine (11) as a yellow solid (0.367 g, 1.21 mmol, 88.0% yield). $^1$H NMR (600 MHz, DMSO-d$_6$, 300K): δ 8.88 (1H, br s), 8.12 (1H, br s), 8.06-8.09 (2H, m), 7.96-7.93 (3H, m), 7.41 (2H, d, J=8.3 Hz), 6.89 (1H, d, J=3.6 Hz), 3.96 (3H, s), 2.33 (3H, s). 13C{1H} NMR (151 MHz, DMSO-d6, 300K): δ 149.2, 146.5, 134.2, 132.5, 130.9, 129.5, 128.8, 127.4, 126.2, 125.5, 105.8, 56.6, 21.5. HRMS (ESI) m/z [M+H]$^+$: molecular ion calculated for C$_{15}$H$_{15}$N$_2$O$_3$S: 303.0798, found 303.0808, error 3.2 ppm.

Example 3

An alternative preparation of Steps 1-3 where the isolation of the Step 1 and 2 intermediates is avoided is shown below:

Steps 1-3: Preparation of 2-((ethoxycarbonyl)(furan-2-ylmethyl)amino)acetic acid (5)

Furfurylamine (1) (100 g, 1.03 mol) and triethylamine (430 mL, 3.09 mol, 3.0 eqvv) were dissolved in toluene (670 ml, 6.7 vols.). Ethyl chloroacetate (2) (126 mL, 1.18 mol, 1.15 eqv) was added and the mixture was heated to 65° C. for 26 hours. The reaction mixture was cooled to 20° C., and filtered, then the precipitated solids were washed with toluene (200 ml, 2 vol).

To the combined filtrates, triethylamine (100 mL, 0.72 mol, 0.70 eqvv) was added and the mixture cooled to 5° C. Ethyl chloroformate (111.7 g, 1.03 mol, 1.0 eqvv) was added dropwise (reaction temperature maintained below 15° C.) then mixture was stirred at 25° C. for 8 hours. The mixture was filtered and the precipitated solids were washed with toluene (300 ml, 3 vol).

The combined filtrates were cooled down to 10° C. and 2M aqueous potassium hydroxide (566 ml, 5.66 vol) was slowly added. The biphasic solution was stirred at 25° C. for 48 hours The phases were separated and the organic layer was washed with water (200 ml, 2 vol). The combined aqueous phases were then cooled down to 5° C. 37% hydrochloric acid (101 g) was added slowly to a final pH in the range 2-3. The mixture was extracted with tert-butylmethylether (3×600 ml, 3×6 vol) The combined organic layers were dried over MgSO4, filtered and evaporated to afford 2-((ethoxycarbonyl)(furan-2-ylmethyl)amino)acetic acid (5) (153 g) as a brown oil. $^1$H NMR (600 MHz, DMSO-d$_6$, 300K). [Note: at this temperature, two rotamers (A+B) in an approximately equal ratio are visible. They are due to restricted rotation of the tertiary amide: δ 7.60-7.58 (A+B, 1H, m), 6.40-6.38, (A+B, 1H, m), 6.36 (A, 1H, d, J=3.0 Hz), 6.34 (B, 1H, d, J=3.0 Hz), 4.44 (A+B, 2H, s), 4.08 (B, 2H, q, J=7.0 Hz), 4.03, (A, 2H, q, J=7.0 Hz) 3.83 (B, 2H, s), 3.82 (A, 2H, s), 1.20 (B, 3H, t, J=7.0 Hz), 1.14 (A, 3H, t, J=7.0 Hz). $^{13}$C{$^1$H} NMR (151 MHz, DMSO-d$_6$, 300K): δ 171.1 (A), 171.0 (B), 156.0 (A), 155.9 (B), 151.2 (B), 151.1 (A), 143.3 (A), 143.2 (B), 110.91 (B), 110.88 (A), 109.1 (A), 108.8 (B), 61.7 (B), 61.6 (A), 61.03 (A), 48.3 (B), 47.9 (A), 44.2 (A), 44.1 (B), 14.94 (B), 14.91 (A). HRMS (ESI) m/z [M+Na]$^+$: molecular ion calculated for C$_{10}$H$_{13}$NNaO$_5$: 250.0686, found 250.0681, error 1.9 ppm.

An alternative preparation of Step 4 where aqueous potassium hydroxide is used in the work-up and material isolated by crystallisation is shown below:

Step 4: Preparation of ethyl 4-oxo-4,5-dihydrofuro[2,3-c]pyridine-6(7H)-carboxylate (6)

2-((Ethoxycarbonyl)(furan-2-ylmethyl)amino)acetic acid (5) (20.0 g, 88 mmol) was dissolved in methylene chloride (200 mL, 10 vols.). Thionyl chloride (7.66 mL, 105 mmol, 1.19 eqvv) and dimethylformamide (0.1 mL, 1.28 mmol, 0.015 eqvv) were added and the mixture was heated at 40° C. for 1 hour then the reaction mixture was cooled to 0° C. Separately, methylene chloride (400 mL, 20 vols.), and aluminium chloride (25.23 g, 189 mmol, 2.15 eqvv) were mixed and heated to reflux for 1 hour then cooled to 0° C. The acid chloride solution prepared above was slowly added to the aluminium chloride mixture over 1 hour. After stirring for 2 hours at 0° C., aluminium chloride (1.17 g. 8.8 mmol, 0.1 eqvv) was added and stirring maintained at 0° C. for a further 30 minutes. 50% potassium hydroxide solution (89 g) was added slowly then the reaction warmed to 38° C. and stirred for 15 h. The reaction mixture was then filtered to remove solids, then the filtrate was dried over MgSO4, then the solvent was evaporated in vacuo to give crude ethyl 4-oxo-4,5-dihydrofuro[2,3-c]pyridine-6(7H)-carboxylate (6) (14 g). A portion of the crude material (6.5 g) was dissolved in isopropanol (6.5 ml, 1 vol) at 80° C., followed by addition of water (30 ml, 4.62 vol), then the mixture cooled to 0° C. After stirring for 1 h, the precipitate was filtered, washed with water (30 ml, 4.62 vol then dried in vacuo to give ethyl 4-oxo-4,5-dihydrofuro[2,3-c]pyridine-6 (7H)-carboxylate (6) (6 g) as an orange solid.). $^1$H NMR (600 MHz, DMSO-d$_6$, 300K). [Note: at this temperature, two rotamers (A+B) in an approximately equal ratio are visible. They are due to restricted rotation of the tertiary amide: δ 7.86 (A+B, 1H, d, J=2.0 Hz), 6.80 (A+B, 1H, d, J=2.0 Hz), 4.81 (A+B, 2H, br s), 4.17 (A+B, 2H, br s), 4.11 (A+B, 2H, q, J=7.1 Hz), 1.21 (A+B, 3H, t, J=7.1 Hz). $^{13}$C{$^1$H} NMR (151 MHz, DMSO-d$_6$, 300K): δ 188.3 (A+B), 163.7 (A), 163.4 (B), 154.6 (A+B), 144.9 (A+B), 119.1 (A+B), 105.9 (A+B), 61.8 (A+B), 51.7 (A), 51.5 (B), 41.3 (A+B), 14.4 (A+B). HRMS (ESI) m/z [M+H]$^+$: molecular ion calculated for C$_{10}$H$_{12}$NO$_4$: 210.0761, found 210.0767, error 3.0 ppm.

An alternative preparation of Step 5 where pyrrolidine is used as a solvent and the reaction is run at ambient temperature as a result is presented below:

Step 5: Preparation of ethyl 4-oxo-4,5-dihydro-1H-pyrrolo[2,3-c]pyridine-6(7H)-carboxylate (7)

Ethyl 4-oxo-4,5-dihydrofuro[2,3-c]pyridine-6(7H)-carboxylate (6) (1.90 g, 9.07 mmol) was dissolved in pyrrolidine (3 mL, 5 vols.) and stirred for 1 h at 20° C. 35% aqueous ammonia in water (7 ml) was added and stirring continued at 20° C. for 4 hours. The mixture was concentrated in vacuo and then the residue was partitioned between ethyl acetate (20 ml, 10.5 vol) and water (20 ml, 10.5 vol). The aqueous layer was separated and extracted with ethyl acetate (3×20 ml, 3×10.5 vol), then the combined extracts were washed with 0.1M hydrochloric acid (25 ml, 13.2 vol), and water (25 ml, 13.2 vol), then dried and concentrated in vacuo to give ethyl 4-oxo-4,5-dihydro-1H-pyrrolo[2,3-c]pyridine-6(7H)-carboxylate (7) as a brown oil. $^1$H NMR (600 MHz, DMSO-$d_6$, 300K). [Note: at this temperature, two rotamers (A+B) in an approximately equal ratio are visible. They are due to restricted rotation of the tertiary amide: δ 11.58 (A, 1H, s), 11.53 (B, 1H, s), 6.87-6.88 (A+B, 1H, m), 6.36 (A+B, 1H, dd, J=2.2 Hz, 2.8 Hz), 4.70 (A+B, 2H, br s), 4.09 (A+B, 2H, q, J=7.1 Hz), 4.06 (A+B, 2H, br s), 1.20 (A+B, 3H, t, J=7.1 Hz). $^{13}$C{$^1$H} NMR (151 MHz, DMSO-$d_6$, 300K): δ 188.0 (A), 187.8 (B), 155.2 (A), 155.1 (B), 140.9 (A), 140.5 (B), 120.8 (A+B), 118.2 (A), 118.0 (B), 104.9 (A+B), 61.9 (A+B), 52.2 (A), 52.0 (B), 41.1 (A), 41.0 (B), 14.9 (A+B). HRMS (ESI) m/z [M+H]$^+$: molecular ion calculated for $C_{10}H_{13}N_2O_3$: 209.0921, found 209.0929, error 3.9 ppm.

Step 8 is the same as for Example 2.

Step 8: Preparation of ethyl 4-oxo-1-tosyl-4,5-dihydro-1H-pyrrolo[2,3-c]pyridine-6(7H)-carboxylate (10)

To a solution of (ethyl 4-oxo-4,5-dihydro-1H-pyrrolo[2,3-c]pyridine-6(7H)-carboxylate) (7) (0.50 g, 2.4 mmol) in methylene chloride (5 mL, 10 vols.) was added triethylamine (0.97 mL, 7.2 mmol, 3 eqv) dropwise at room temperature. To the resulting suspension was added p-toluenesulphonyl chloride (0.46 g, 2.4 mmol, 1 eqv) and 4-dimethylaminopyridine (DMAP) (0.029 g, 0.24 mmol, 0.1 eqv). The reaction mixture was stirred until p-toluenesulphonyl chloride was consumed. The mixture was poured into water (10 mL, 20 vols.) and extracted with methylene chloride (2×5 mL, 2×10 vols.). Combined organic layers were dried over anhydrous magnesium sulphate, filtered and evaporated in vacuo. The crude was purified by flash chromatography on silica gel (10% ethyl acetate in cyclohexane) affording ethyl 4-oxo-1-tosyl-4,5-dihydro-1H-pyrrolo[2,3-c]pyridine-6(7H)-carboxylate (10) as a pale pink solid (0.58 g, 2.0 mmol, 83.0% yield). $^1$H NMR (600 MHz, DMSO-$d_6$, 300K). [Note: at this temperature, two rotamers (A+B) in an approximately equal ratio are visible. They are due to restricted rotation of the tertiary amide: δ 7.96 (A+B, 2H, d, J=8.3 Hz), 7.55-7.53 (A+B, 3H, m), 6.64 (A+B, 1H, d, J=3.5 Hz), 4.98 (A+B, 2H, s), 4.13 (A+B, 2H, br s), 4.07 (A+B, 2H br q, J=7.0 Hz), 2.42 (3H, s), 1.17 (A+B, 3H, br t, J=7.0 Hz). $^{13}$C{$^1$H} NMR (151 MHz, DMSO-$d_6$, 300K): δ 189.1 (A), 188.6 (B), 155.2 (A), 155.0 (B), 147.3 (A+B), 141.1 (A), 140.7 (B), 134.3 (A+B), 131.1 (A+B), 127.7 (A+B), 123.9 (A+B), 122.8 (A+B), 122.6 (B), 108.8 (A+B), 62.3 (A+B), 51.9 (A+B), 41.6 (A), 41.4 (B), 21.6 (A+B), 14.8 (A+B). HRMS (ESI) m/z [M+H]$^+$: molecular ion calculated for $C_{17}H_{19}N_2O_5S$: 363.1009, found 363.1017, error 2.2 ppm.

An alternative preparation of Step 9 where tert-butyl hydroperoxide in decane is used as an oxidant is presented below:

Step 9: Preparation of 4-methoxy-1-(4-methylphenylsulphonyl)-1H-pyrrolo[2,3-c]pyridine (11)

(Ethyl 4-oxo-1-tosyl-4,5-dihydro-1H-pyrrolo[2,3-c]pyridine-6(7H)-carboxylate) (10) (2.00 g, 5.52 mmol) and toluene (24 ml, 12 vol) was charged to reaction vessel then the vessel was inerted using $N_2$. Methane sulphonic acid (0.53 mL, 8.16 mmol, 1.48 eqv) and trimethylorthoformate (1.83 mL, 16.7 mmol, 3.02 eqv) were added inertion was continued for 3 minutes. Methanol (1.1 ml, 27.1 mmol, 4.9 eqvv) and 5.5M tert-butyl hydroperoxide in decane (1.3 mL, 7.15 mmol, 1.3 eqv) were added and the reaction mixture was aged at 35° C. for 18 hours. 2M sodium hydroxide (10 ml, 5 vol) and 0.1M sodium thiosulfate (5 ml, 2.5 vol) were added and the reaction mixture was stirred at 20° C. for 2 hours. The phases were separated and the aqueous layer was extracted with ethyl acetate (2×25 ml, 2×12.5 vol). The combined organic solutions were dried over $MgSO_4$ and concentrated in vacuo. The residue was partitioned between 2M hydrochloric acid (10 ml, 5 vol) and tert-butylmethylether (10 ml, 5 vol). The aqueous layer was separated and neutralised by addition of sodium hydroxide, then extracted with tert-butylmethylether (3×10 ml, 3×5 vol). The combined organic extracts were dried over $MgSO_4$ and concentrated in vacuo to give 4-methoxy-1-(4-methylphenylsulphonyl)-1H-pyrrolo[2,3-c]pyridine (11) (0.91 g, 54% th).). $^1$H NMR (600 MHz, DMSO-$d_6$, 300K): δ 8.88 (1H, br s), 8.12 (1H, br s), 8.06-8.09 (2H, m), 7.96-7.93 (3H, m), 7.41 (2H, d, J=8.3 Hz), 6.89 (1H, d, J=3.6 Hz), 3.96 (3H, s), 2.33 (3H, s). 13C{1H} NMR (151 MHz, DMSO-d6, 300K): δ 149.2, 146.5, 134.2, 132.5, 130.9, 129.5, 128.8, 127.4, 126.2, 125.5, 105.8, 56.6, 21.5. HRMS (ESI) m/z [M+H]$^+$: molecular ion calculated for $C_{15}H_{15}N_2O_3S$: 303.0798, found 303.0808, error 3.2 ppm.

Even though the depicted 5-membered ring in Formula IV contains a Nitrogen atom, we have found that our cost of goods is lower starting with a five-membered ring that contains an Oxygen.

What is claimed is:

1. A method for the preparation of a compound of Formula IV

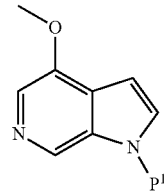

Formula IV wherein $P^1$ is H or a suitable protecting group;
comprising the preparation of a compound of Formula I

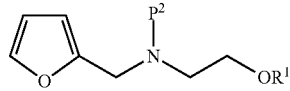

Formula I wherein P² is H or a suitable protecting group and R¹ is H or $C_{1-6}$alkyl, and further comprising the conversion of the compound of Formula I to a compound of Formula II

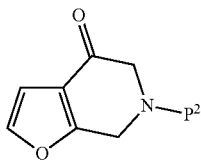

Formula II wherein each P² is independently H or a suitable protecting group.

2. The method of claim 1 further comprising the conversion of a compound of Formula II into a compound of Formula III

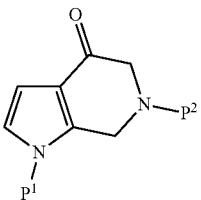

Formula III wherein each P¹ and P² are independently H or a suitable protecting group.

3. A method according to claim 1 wherein R¹ is H or $C_{1-3}$alkyl.

4. The method of claim 3 wherein R¹ is H or ethyl.

5. A method according to claim 1 wherein P¹ is H or a sulphonyl group.

6. The method of claim 5 wherein P¹ is H or a mesylate, besylate, or tosylate group.

7. A method according to claim 1 wherein P² is H or an alkyloxycarbonyl, aryloxycarbonyl, acetyl optionally substituted with 1-3 halogens, sulphonyl, alkyl, or benzyl group.

8. The method of claim 1 wherein P² is H or —C(O)—O—$C_{1-4}$alkyl, —C(O)—$C_{1-4}$alkyl, —C(O)—$C_{1-4}$haloalkyl, mesylate, besylate, tosylate, $C_{1-6}$alkyl, or —$C_{1-6}$alkyl-aryl.

9. A method for preparation of Temsavir, Fostemsavir, or a pharmaceutically acceptable salt thereof, comprising:

preparation of a compound of Formula I

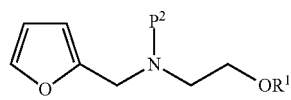

Formula I wherein P² is H or a suitable protecting group and R¹ is H or $C_{1-6}$alkyl; and conversion of the compound of Formula I to a compound of Formula II

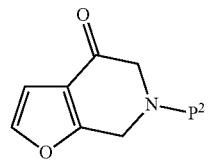

Formula II wherein each P² is independently H or a suitable protecting group.

10. The method of claim 9, further comprising conversion of the compound of Formula II into a compound of Formula III

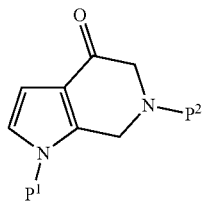

Formula III wherein each P¹ and P² are independently H or a suitable protecting group.

11. The method of claim 10, further comprising conversion of the compound of Formula III into a compound of Formula IV

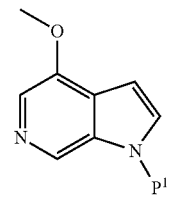

Formula IV wherein P¹ is H or a suitable protecting group.

12. The method of claim 11, further comprising conversion of the compound of Formula IV into Temsavir, Fostemsavir, or a pharmaceutically acceptable salt thereof.

13. The method of claim 9 wherein R¹ is H or $C_{1-3}$alkyl.

14. The method of claim 13 wherein R¹ is H or ethyl.

15. The method of claim 10 wherein P¹ is H or a sulphonyl group.

16. The method of claim 15 wherein P¹ is H or a mesylate, besylate, or tosylate group.

17. The method of claim 9 wherein P² is H or an alkyloxycarbonyl, aryloxycarbonyl, acetyl optionally substituted with 1-3 halogens, sulphonyl, alkyl, or benzyl group.

18. The method of claim 9, wherein P² is H or —C(O)—O—$C_{1-4}$alkyl, —C(O)—$C_{1-4}$alkyl, —C(O)—$C_{1-4}$haloalkyl, mesylate, besylate, tosylate, $C_{1-6}$alkyl, or —$C_{1-6}$alkyl-aryl.

* * * * *